(12) United States Patent
Hilse et al.

(10) Patent No.: US 11,291,468 B2
(45) Date of Patent: Apr. 5, 2022

(54) ATHERECTOMY SYSTEM ADAPTED TO FREE A STUCK ATHERECTOMY BURR

(71) Applicant: BOSTON SCIENTIFIC SCIMED, INC., Maple Grove, MN (US)

(72) Inventors: Mark A. Hilse, Ham Lake, MN (US); Corydon Carlson, Stillwater, MN (US); David Gordon Spangler, New Richmond, WI (US); Daniel Frank Massimini, Brooklyn Park, MN (US); Laszlo Trent Farago, Hudson, WI (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 213 days.

(21) Appl. No.: 16/444,789

(22) Filed: Jun. 18, 2019

(65) Prior Publication Data
US 2020/0397464 A1    Dec. 24, 2020

(51) Int. Cl.
*A61B 17/22*    (2006.01)
*A61B 17/3207*    (2006.01)
(Continued)

(52) U.S. Cl.
CPC ...... *A61B 17/320758* (2013.01); *A61B 17/22* (2013.01); *A61M 25/09* (2013.01);
(Continued)

(58) Field of Classification Search
CPC ............ A61B 17/320758; A61B 17/22; A61B 2017/00199; A61B 2017/22038; A61B 2017/22094; A61B 2017/320741; A61B 2017/00119; A61B 2017/00075; A61B 2017/00017; A61B 2090/08021; A61B 2017/00398; A61B 2090/066; A61B 17/3207; A61B 17/320725; A61B 17/320783; A61M 25/09; A61F 2/01
See application file for complete search history.

(56) References Cited

U.S. PATENT DOCUMENTS

| | | |
|---|---|---|
| 2001/0004700 A1 | 6/2001 | Honeycutt et al. |
| 2008/0039823 A1 | 2/2008 | Shimogami et al. |

(Continued)

FOREIGN PATENT DOCUMENTS

| | | |
|---|---|---|
| WO | 2010056714 A1 | 5/2010 |
| WO | 2019168784 A1 | 9/2019 |

OTHER PUBLICATIONS

International Search Report and Written Opinon dated Sep. 7, 2020 for International Application No. PCT/US2020/038145.

*Primary Examiner* — Vi X Nguyen
(74) *Attorney, Agent, or Firm* — Seager, Tufte & Wickhem, LLP (57) ABSTRACT

An atherectomy system includes a drive mechanism adapted to rotatably actuate an atherectomy burr and a controller that is adapted to operate the drive mechanism in a first operating mode in which the atherectomy burr is operated at a speed reference and with a predetermined torque limit. The controller is adapted to determine when the atherectomy burr becomes stuck while in the first operating mode and is further adapted to, when the atherectomy burr becomes stuck, operate the drive mechanism in a second operating mode that is different from the first operating mode.

19 Claims, 7 Drawing Sheets

(51) Int. Cl.
  *A61M 25/09* (2006.01)
  *A61B 17/00* (2006.01)
  *A61F 2/01* (2006.01)

(52) U.S. Cl.
  CPC ............... *A61B 2017/00199* (2013.01); *A61B 2017/22038* (2013.01); *A61B 2017/22094* (2013.01); *A61B 2017/320741* (2013.01); *A61F 2/01* (2013.01)

(56) References Cited

U.S. PATENT DOCUMENTS

| | | | |
|---|---|---|---|
| 2011/0213391 A1* | 9/2011 | Rivers | A61B 17/320758 606/159 |
| 2012/0095461 A1* | 4/2012 | Herscher | A61B 18/1206 606/45 |
| 2015/0201956 A1 | 7/2015 | Higgins et al. | |
| 2019/0175211 A1 | 6/2019 | Carlson et al. | |

\* cited by examiner

ATHERECTOMY SYSTEM ADAPTED TO FREE A STUCK ATHERECTOMY BURR

TECHNICAL FIELD

The present disclosure pertains to medical devices, and methods for manufacturing and using medical devices. More particularly, the disclosure is directed to devices and methods for removing occlusive material from a body lumen. Further, the disclosure is directed to an atherectomy device for forming a passageway through an occlusion of a body lumen, such as a blood vessel.

BACKGROUND

Many patients suffer from occluded arteries and other blood vessels which restrict blood flow. Occlusions can be partial occlusions that reduce blood flow through the occluded portion of a blood vessel or total occlusions (e.g., chronic total occlusions) that substantially block blood flow through the occluded blood vessel. In some cases a stent may be placed in the area of a treated occlusion. However, restenosis may occur in the stent, further occluding the vessel and restricting blood flow. Revascularization techniques include using a variety of devices to pass through the occlusion to create or enlarge an opening through the occlusion. Atherectomy is one technique in which a catheter having a cutting element thereon is advanced through the occlusion to form or enlarge a pathway through the occlusion. A need remains for alternative atherectomy devices to facilitate crossing an occlusion.

SUMMARY

This disclosure provides design, material, manufacturing method, and use alternatives for medical devices. For example, an atherectomy system includes an atherectomy burr and a drive mechanism that is adapted to rotatably actuate the atherectomy burr. A controller is adapted to operate the drive mechanism in a first operating mode in which the atherectomy burr is operated at a speed reference and with a predetermined torque limit. The controller is adapted to determine when the atherectomy burr becomes stuck while in the first operating mode. When the atherectomy burr becomes stuck, the controller is further adapted to operate the drive mechanism in a second operating mode that is different from the first operating mode.

Alternatively or additionally, the second operating mode may include operating the atherectomy burr at a position reference instead of the speed reference.

Alternatively or additionally, when in the second operating mode, the controller may be further adapted to alternate between driving the drive mechanism in a first rotational direction and driving the drive mechanism in a second rotational direction opposite that of the first rotational direction.

Alternatively or additionally, when in the second operating mode, the controller may be further adapted to drive the drive mechanism in the first rotational direction for a first distance and to drive the drive mechanism in the second rotational direction for a second distance that is different from the first distance.

Alternatively or additionally, the first distance and the second distance may be selected based on a known spring constant of the drive mechanism.

Alternatively or additionally, when in the second operating mode, the controller may be further adapted to periodically adjust the first distance and/or the second distance.

Alternatively or additionally, when in the second operating mode, the controller may be further adapted to periodically adjust a time period between driving the drive mechanism in the first rotational direction and driving the drive mechanism in the second rotational direction.

Alternatively or additionally, the second operating mode may include operating the atherectomy burr at low speed at a temporary torque value that exceeds the predetermined torque limit of the first operating mode while the atherectomy burr is not moving.

Alternatively or additionally, the temporary torque value may exceed the predetermined torque limit of the first operating mode by ten percent.

Alternatively or additionally, the temporary torque value may exceed the predetermined torque limit of the first operating mode by twenty percent.

Alternatively or additionally, when in the second operating mode, the controller may revert back to the first operating mode as soon as the atherectomy burr begins to move.

Alternatively or additionally, the second operating mode may further include temporarily exceeding the predetermined torque limit of the first operating mode while alternating driving the drive mechanism in a first rotational direction and driving the drive mechanism in a second rotational direction opposite that of the first rotational direction.

As another example, an atherectomy system includes an atherectomy burr and a drive mechanism that is adapted to rotatably actuate the atherectomy burr. A controller is adapted to operate the drive mechanism using a speed reference, and is adapted to determine when the atherectomy burr becomes stuck. The controller is further adapted to, when the atherectomy burr becomes stuck, switch to a stuck burr mode in which the controller uses a position reference in alternating between driving the drive mechanism in a first rotational direction and driving the drive mechanism in a second rotational direction opposite that of the first rotational direction.

Alternatively or additionally, when in the stuck burr mode, the controller may be further adapted to drive the drive mechanism in the first rotational direction for a first distance and to drive the drive mechanism in the second rotational direction for a second distance that is different from the first distance.

Alternatively or additionally, the first distance and the second distance may be selected based on a known spring constant of the drive mechanism.

Alternatively or additionally, when in the stuck burr mode, the controller may be further adapted to periodically adjust the first distance and/or the second distance.

Alternatively or additionally, when in the stuck burr mode, the controller may be further adapted to periodically adjust a time period between driving the drive mechanism in the first rotational direction and driving the drive mechanism in the second rotational direction.

As another example, an atherectomy system includes an atherectomy burr and a drive mechanism that is adapted to rotatably actuate the atherectomy burr. A controller is adapted to operate the drive mechanism using a speed reference and with a predetermined torque limit, and is adapted to determine when the atherectomy burr becomes stuck. The controller is further adapted to, when the atherectomy burr becomes stuck, to operate the drive mechanism at low speed at a temporary torque value that exceeds the predetermined torque limit while the atherectomy burr is not moving.

Alternatively or additionally, the temporary torque value may exceed the predetermined torque limit up to twenty percent.

Alternatively or additionally, the controller may revert to operating the drive mechanism in accordance with the speed reference and the predetermined torque limit as soon as the atherectomy burr begins to move.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Many patients suffer from occluded arteries, other blood vessels, and/or occluded ducts or other body lumens which may restrict bodily fluid (e.g. blood, bile, etc.) flow. Occlusions can be partial occlusions that reduce blood flow through the occluded portion of a blood vessel or total occlusions (e.g., chronic total occlusions) that substantially block blood flow through the occluded blood vessel. Revascularization techniques include using a variety of devices to pass through the occlusion to create or enlarge an opening through the occlusion. Atherectomy is one technique in which a catheter having a cutting element thereon is advanced through the occlusion to form or enlarge a pathway through the occlusion. Ideally, the cutting element excises the occlusion without damaging the surrounding vessel wall and/or a previously implanted stent where restenosis has occurred. However, in some instances the cutting element may be manipulated and/or advanced such that it contacts the vessel wall and/or the stent. Therefore, it may be desirable to utilize materials and/or design an atherectomy device that can excise an occlusion without damaging the surrounding vessel and/or a previously implanted stent where restenosis has occurred. Additionally, it may be desirable that a cutting element be useful in removing hard occlusive material, such as calcified material, as well as softer occlusive material. The methods and systems disclosed herein may be designed to overcome at least some of the limitations of previous atherectomy devices while effectively excising occlusive material. For example, some of the devices and methods disclosed herein may include cutting elements with unique cutting surface geometries and/or designs.

Figure 1:
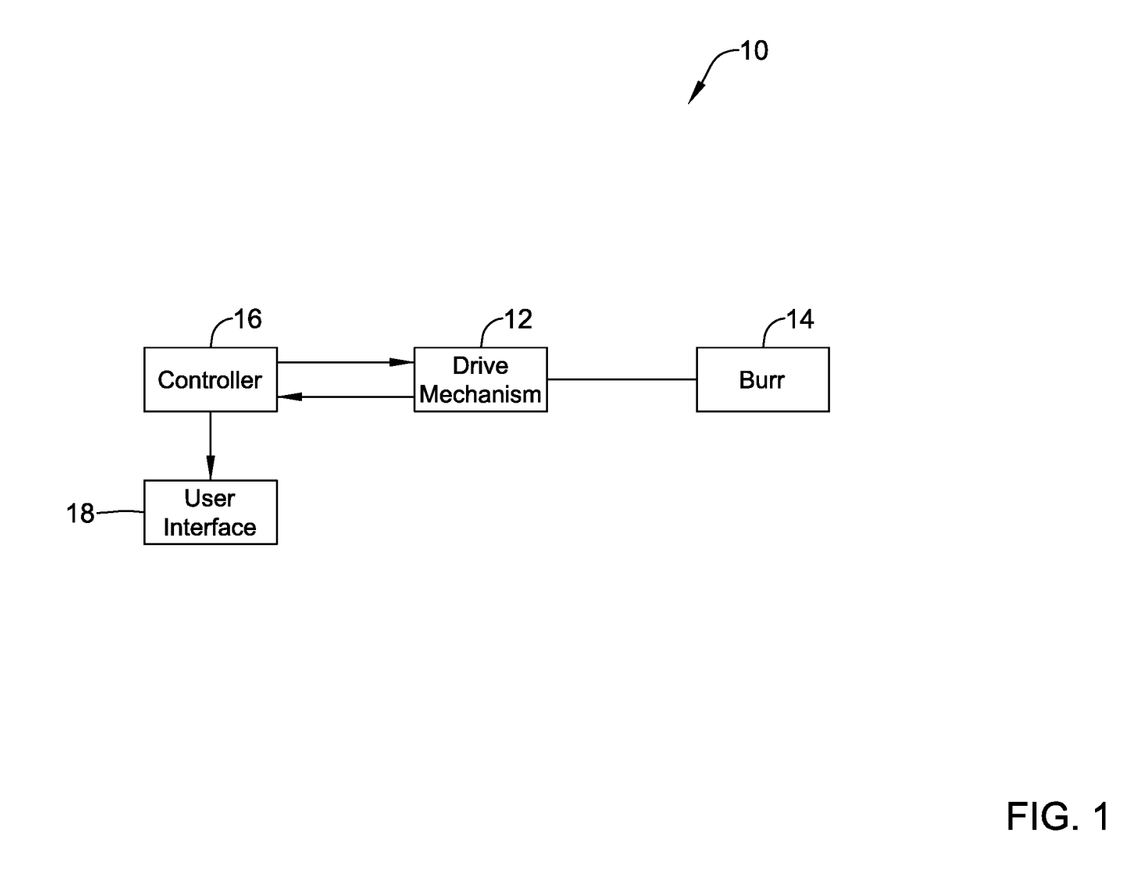
FIG. 1 is a schematic block diagram of an example atherectomy system.

FIG. 1 is a schematic block diagram of an example atherectomy system 10 that includes a drive mechanism 12 that is adapted to rotatably actuate an atherectomy burr 14. The atherectomy system 10 includes a controller 16 that is adapted to regulate operation of the drive mechanism 12. In some cases, the atherectomy system 10 may include a user interface 18 that may be operably coupled to the controller 16 such that the controller 16 is able to display information regarding the performance of the drive mechanism 12. This information may, for example, include one or more of an instantaneous speed of the drive mechanism 12, an instantaneous torque being experienced by the atherectomy burr 14, and the like. In some instances, the atherectomy system 10 may not include the user interface 18. In some cases, the atherectomy burr 14 may also be referred to as being or including a cutting head or a cutting member, and these terms may be used interchangeably.

Figure 2:
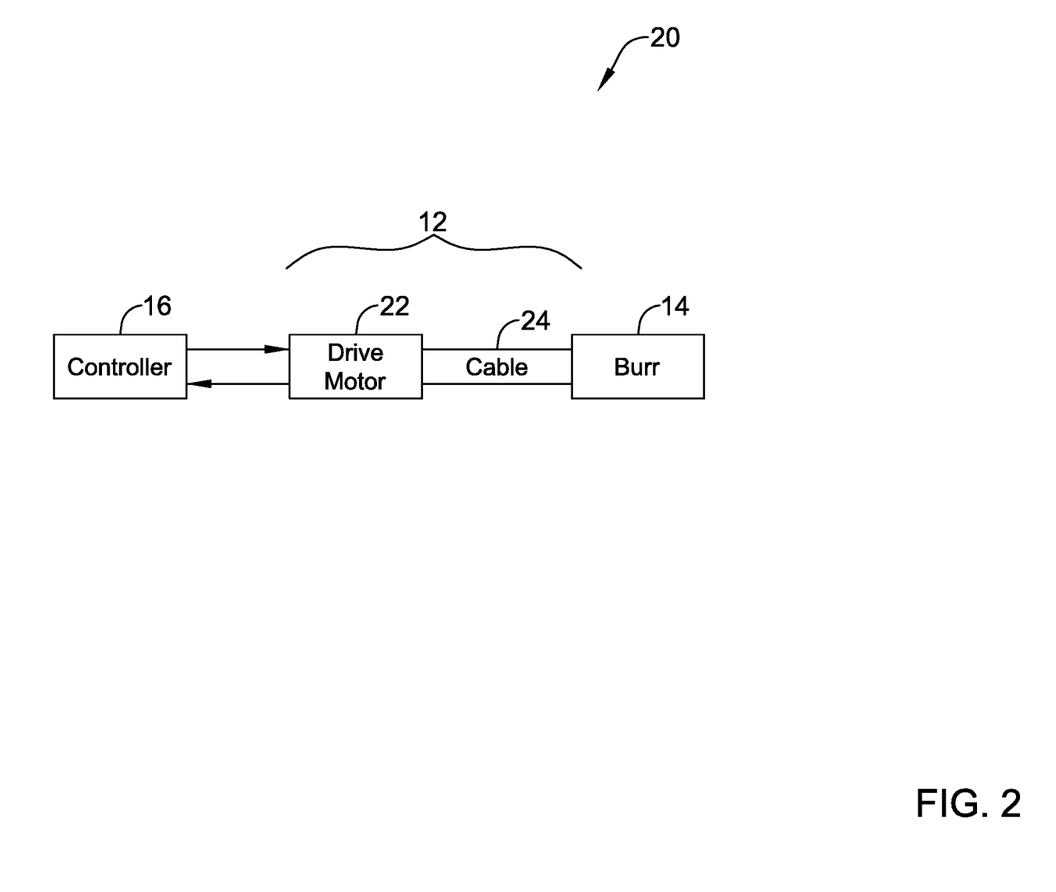
FIG. 2 is a schematic block diagram of an example atherectomy system.

FIG. 2 is a schematic block diagram of an example atherectomy system 20 in which the drive mechanism 12 may include a drive motor 22 and a drive cable 24 that is operably coupled with the drive motor 22 as well as the atherectomy burr 14. In some cases, features of the atherectomy system 20 may be combined with features of the atherectomy system 10. In some cases, the atherectomy system 20 may also include a handle (not shown).

Figure 3:
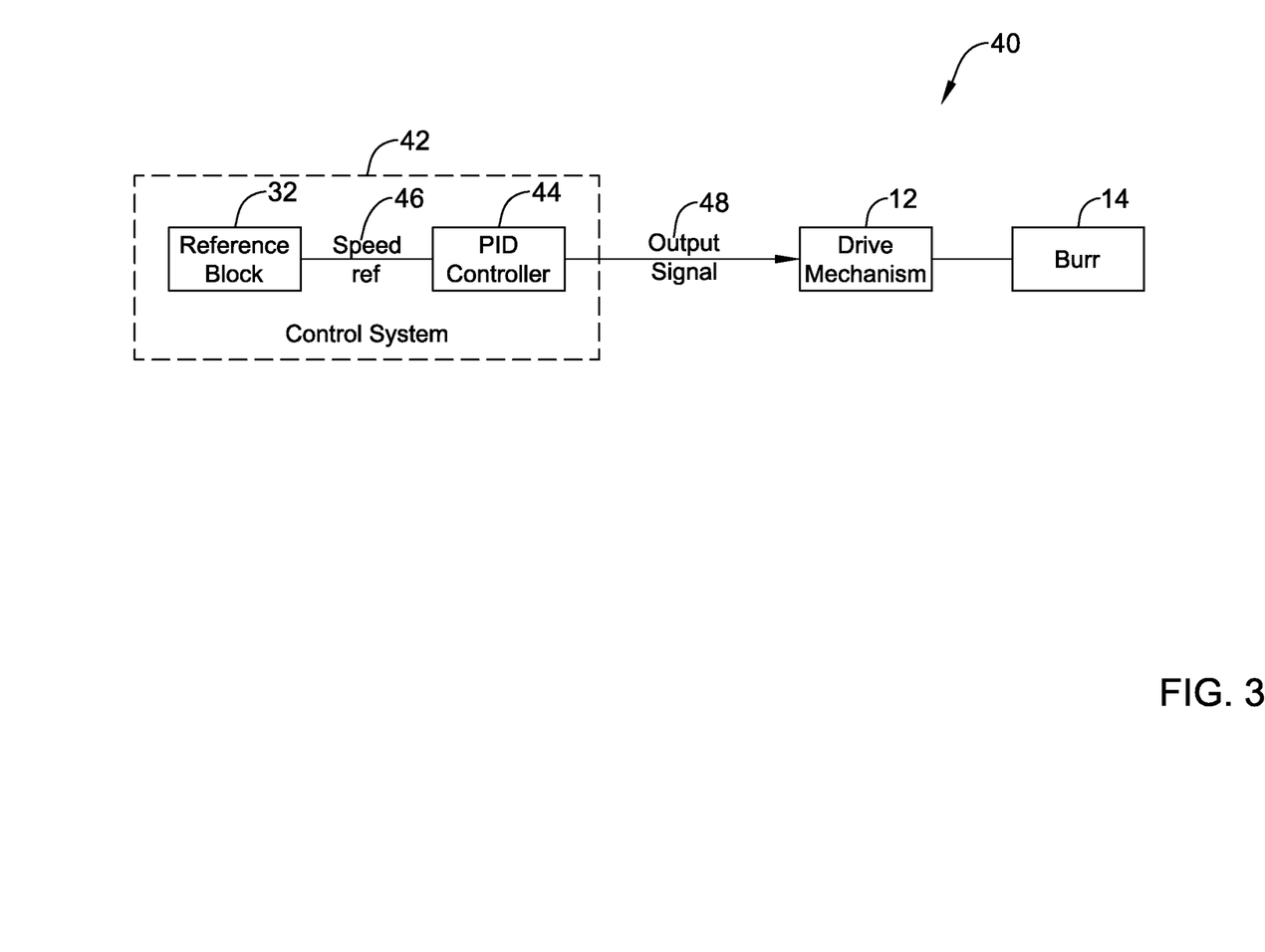
FIG. 3 is a schematic block diagram of an example atherectomy system.

FIG. 3 is a schematic block diagram of an example atherectomy system 40 that includes a control system 42 that is adapted to regulate operation of the drive mechanism 12 in order to rotatably actuate the atherectomy burr 14. In some cases, features of the atherectomy system 40 may be combined with one or more of the atherectomy system 10 and the atherectomy system 20. The control system 42 may include a reference block 32 as well as a Proportional Integral Derivative (PID) controller 44 that is operably coupled to the reference block 32. In some cases, the reference block 32 may determine a speed reference 46 that is selectable between a nominal value, a negative value and zero. In some instances, the PID controller 44 may be further adapted to add an offset value to the speed reference 46 received from the reference block 32, although in some cases, the reference block 32 may add the offset value. The PID controller 44 may be further adapted to provide a reduction in motor speed of the drive mechanism 12 that is greater than what would otherwise normally occur in response to an increasing torque experienced at the atherectomy burr 14.

Figure 4:
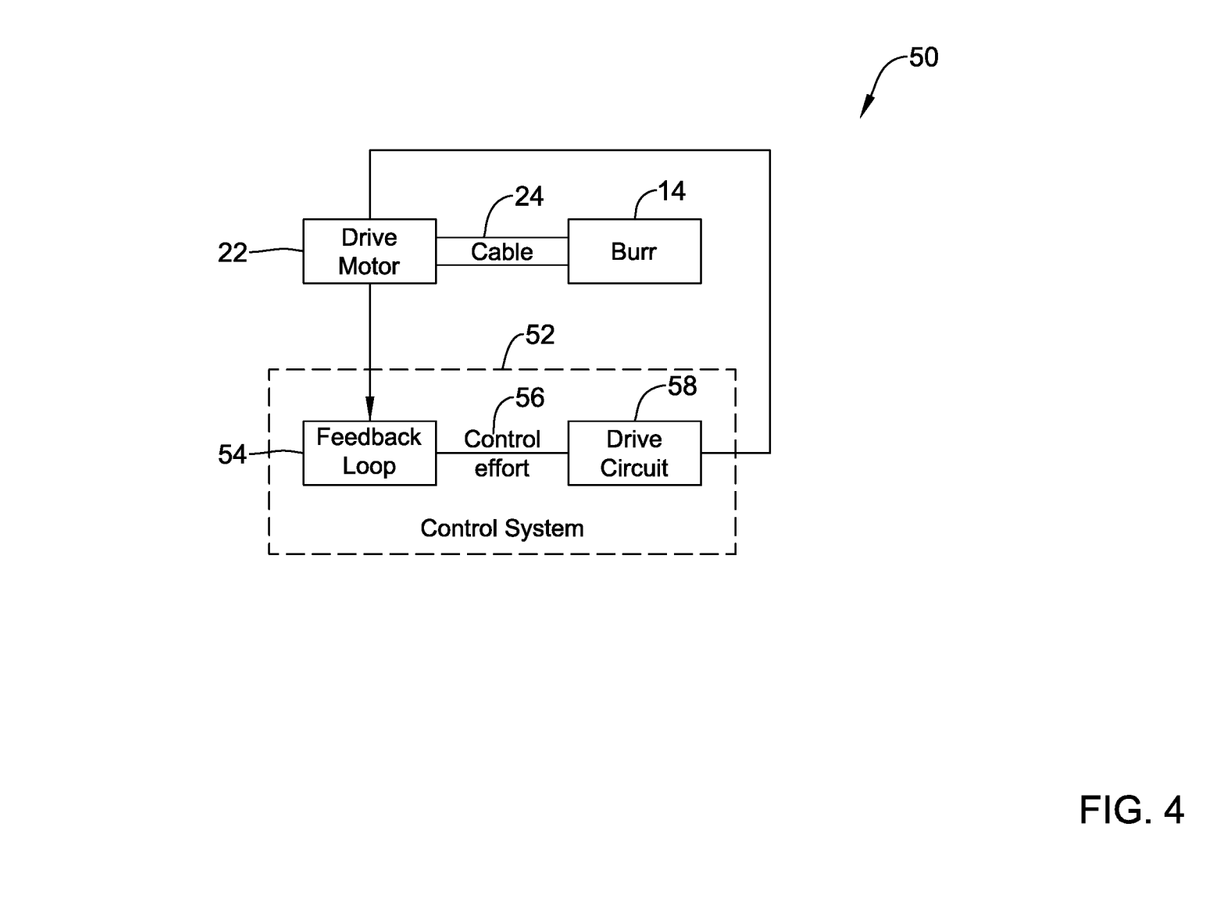
FIG. 4 is a schematic block diagram of an example atherectomy system.

FIG. 4 is a schematic block diagram of an example atherectomy system 50 that includes a control system 52 that is adapted to regulate operation of the drive motor 22 in order to rotatably actuate the atherectomy burr 14. In some cases, features of the atherectomy system 50 may be combined with one or more of the atherectomy system 10, the atherectomy system 20 or the atherectomy system 40. The control system 52 is operably coupled to the drive motor 22 and includes a feedback loop 54 that is adapted to monitor performance of the drive motor 22 and to output a control effort signal 56. A drive circuit 58 is adapted to receive the control effort signal 56 and to regulate operation of the drive motor 22 in accordance with the control effort signal 56.

In some cases, the feedback loop 54 may include a reference block for determining a speed reference and a Proportional Integral Derivative (PID) controller that is operably coupled to the reference block for receiving the speed reference, the PID controller adapted to utilize the speed reference, a Proportional (P) gain value, an Integral (I) gain value and a Derivative (D) gain value in determining the control effort signal. In some cases, the feedback loop 54 may be adapted to add an offset value to a reference signal provided to the reference loop 54 in order to accurately hold speed of the drive motor 22 during a no-load situation. In some instances, for example if the atherectomy burr 14 becomes stuck, the control system 52 may be further adapted to increase the torque provided by the drive motor 22 until a torque threshold is reached for a brief period of time, and to subsequently direct the drive motor 22 to reverse at a slow speed in order to unwind energy in the drive mechanism.

Figure 5:
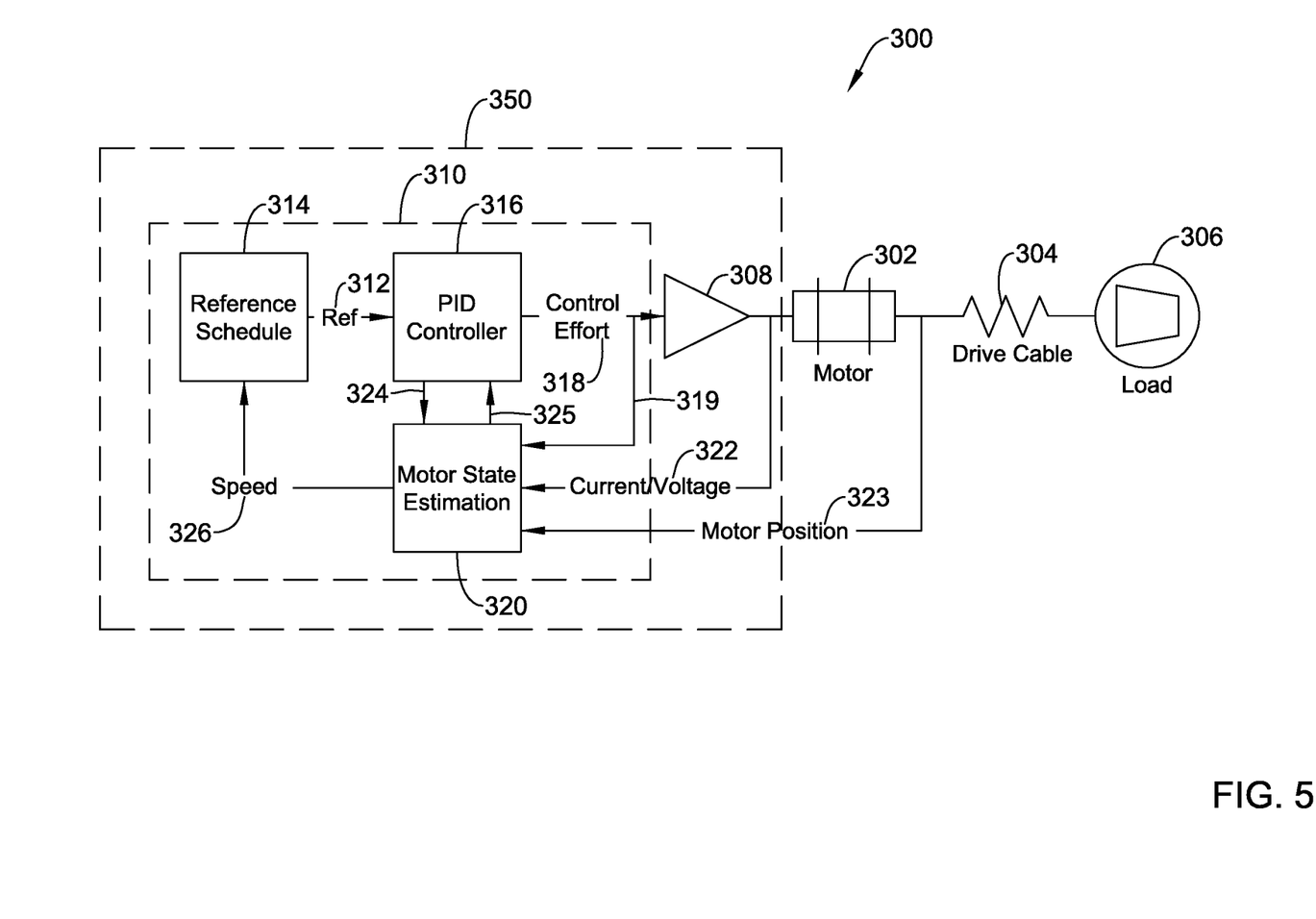
FIG. 5 is a schematic block diagram of an example atherectomy system.

FIG. 5 is a schematic block diagram of an example atherectomy system 300. In some cases, the atherectomy system 300 may be considered as being an example of the atherectomy system 10, 20, 40 or 50. In some instances, features of the atherectomy system 300 may be combined with features of any of the atherectomy systems 10, 20, 40 or 50, for example. The atherectomy system 300 includes a motor 302 that drives a drive cable 304 which itself engages a load 306. The load 306 represents an atherectomy burr, for example. The motor 302 is controlled by a drive circuitry 308 which may be considered as being an example of or otherwise incorporated into the drive motor 22 (FIG. 2) and/or the controller 16 (FIGS. 1-2), for example. In some cases, the motor 302 may be sized, relative to the weight and other dimensions of the atherectomy system 300, to be capable of accelerating the atherectomy burr to full speed in less than 3 seconds, or in some cases in less than 2 seconds. As an example, the motor 302 may be rated for at least 60 watts. In a particular example, the motor 302 may be rated for about 80 watts. These are just examples.

The drive circuitry 308 receives an input from a feedback portion 310. In some cases, the feedback portion 310 begins with a reference input 312 from a reference schedule block 314, which provides the reference input 312 to a PID controller 316. In some cases, the reference schedule block 314 may be configured to accept additional inputs, such as from a user and/or from additional sensors not illustrated. As an example, if the device has been running for too long of a period of time, the reference schedule block 314 may reduce the speed reference in order to prevent overheating. A PID controller is a controller that includes a (P) proportional portion, an (I) integral portion and a (D) derivative portion. The PID controller 316 outputs a control effort value or reference current 318 to the drive circuitry 308. A motor state estimation block 320 receives a current/voltage signal 322 and a motor position signal 323 from the drive circuitry 308 and receives state feedback 324 from the PID controller 316. The motor state estimation block 320 provides a state feedback signal 325 back to the PID controller 316.

The motor state estimation block 320 outputs a speed value 326 back to the reference schedule block 314. While the feedback from the motor state estimation block 320 to the reference schedule block 314 is shown as being a speed value, in some cases the feedback may additionally or alternatively include one or more of position, torque, voltage or current, and in some cases may include the derivative or integral of any of these values. In some cases, the motor state estimation block 320 may instead receive a signal 323 that represents speed, instead of position (as illustrated). The motor position signal 323 may be an indication of relative rotational position of an output shaft of the motor 302, and thus an indication of relative rotational position of the load 306, which if tracked over time may provide an indication of speed.

In some cases, the drive circuitry 308 and the feedback loop 310 may in combination be considered as forming a controller 350 that is adapted to determine an estimated torque at the atherectomy burr (the load 306 as shown in FIG. 5). The controller 350 may be considered as being an example of the controller 16 (FIG. 1). In some cases, the controller 350 may be considered as including only some elements of the drive circuitry 308 and the feedback loop 310. In some instances, some of the features and functions of the controller 350 may take place in the motor state estimation block 320. It will be appreciated that while FIG. 5 shows various components as standalone components, in some cases the functions of one or more of the components may actually be spread between separate components. In some instances, the functions of one or more of the components may be combined into one or more components.

If the estimated torque at the load 306 becomes too high, this may be an indication that the burr is getting stuck. In order to protect against possible damage to the drive cable 304, and to protect against possible injury to the patient, the atherectomy system 300 may be adapted to stop or even reverse operation of the atherectomy system 300 if the estimated torque meets or exceeds a predetermined torque threshold. It will be appreciated that the actual value of the predetermined torque threshold may vary, depending on the mechanics of the atherectomy system 300, but may be set at a level low enough to prevent damage and injury, but not set so low as to engender too many false alarms caused by minor and/or temporary torque increases that are not caused by the load 306 becoming stuck. For example, the instantaneous torque may vary by small amounts as the atherectomy system 300 progresses through the patient's vasculature. Accordingly, the controller 350 may be adapted to calculate an estimated torque at the load 306 and to compare the estimated torque at the load 306 to the torque threshold. If the estimated torque meets or exceeds the torque threshold, the atherectomy system 300 may stop or even reverse the drive mechanism (the drive motor 302 and the drive cable 304, for example).

Figure 6:
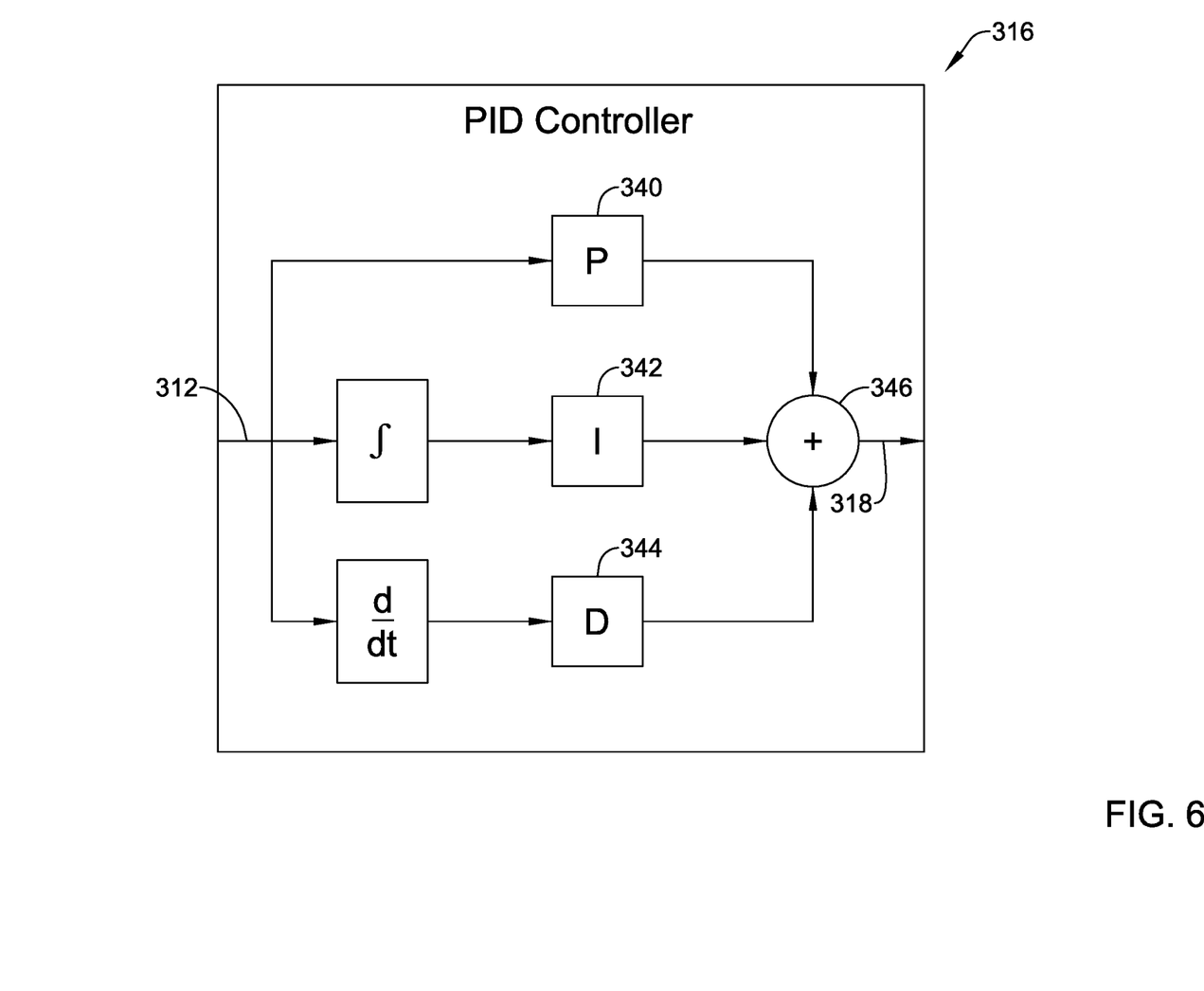
FIG. 6 is a schematic diagram of an example PID controller usable in the example atherectomy systems of FIGS. 1 through 5.

FIG. 6 is a schematic block diagram of the PID controller 316, which may be considered as being an example of the PID controller 44 shown in FIG. 3. An error signal 312, which is representative of an error between a desired value and an actual value, enters the PID controller 316. The PID controller 316 calculates a P term 340, which is proportional to the error. The PID controller 316 calculates an I term 342, which is an integral of the error and a D term 344, which is a derivative of the error. These terms are added together at a summation point 346, resulting in an output of the control effort signal 318.

In some instances, the atherectomy system 300 may be considered as having a first operating mode and a second operating mode. The first operating mode may be considered as a normal operating mode, in which the atherectomy system 300 operates using a speed reference, and with a predetermined torque threshold or limit. As long as the load 306 (the atherectomy burr) is not stuck, i.e., seems to be rotating at a speed close to that expected in response to the rotation of the drive cable 304, the controller 350 will operate in the first operating mode. However, if the controller 350 determines that the load 306 (the atherectomy burr) has become stuck, the controller 350 may instead operate in a second operating mode. In the second operating mode, the atherectomy system 300 may operate differently than in the first operating mode. In some instances, the second operating mode may correspond to a "stuck burr" mode in which the controller 350 is trying to facilitate freeing the stuck burr.

In some cases, the controller 350 will switch to using a position reference instead of a speed reference. In this situation, the controller 350 may alternate between driving the drive mechanism (the drive motor 302 and the drive cable 304, for example) in a first rotational direction and driving the drive mechanism in a second rotational direction that is opposite that of the first rotational direction. In some cases, the controller 350 may drive the drive mechanism in the first rotational direction for a first distance and to drive the drive mechanism in the second rotational direction for a second distance that is different from the first distance. It will be appreciated that the relative distance, or number of rotations of the drive motor 302 in each direction may be different in order to accommodate the spring constant of the drive cable 304. As noted previously, the drive cable 304 may be modeled as a spring. As such, it will be appreciated that rotating the drive cable 304 in one direction may tend to "wind" the spring while rotating the drive cable 304 in the opposing direction will tend to "unwind" the spring. In some cases, for example, the first distance and the second distance may be selected based upon a known spring constant of the drive mechanism.

Figure 7:
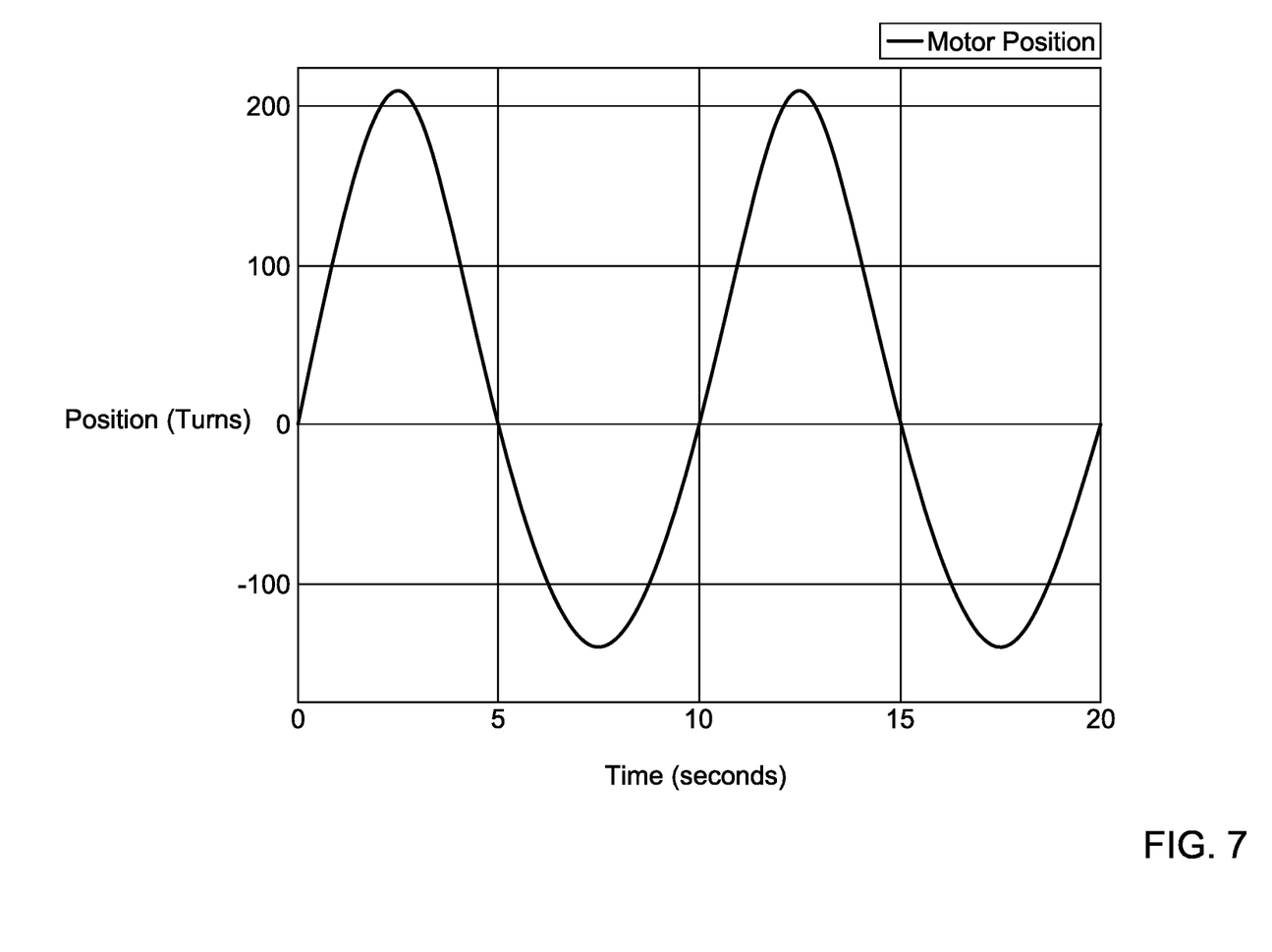
FIG. 7 is a graphical representation of an example motor position reference usable while the atherectomy burr may be jammed.

This is illustrated for example in FIG. 7, which is a graphical representation of using a position reference instead of a speed reference. The X axis represents time while the Y axis represents position. As shown, the Y axis represents a number of motor rotations, with positive numbers representing motor rotations in one direction and negative numbers representing motor rotations in a second, opposing direction. It will be appreciated that by alternating between rotating in a first direction and rotating in a second direction, an oscillation may be achieved. In some cases, an oscillation may assist in freeing a stuck burr. The graph also illustrates how the drive motor 302 may drive further (more turns) in one direction than in the other direction.

In some cases, the distances (number of rotations) traveled in each direction may remain constant. In some instances, it is contemplated that the controller 350 may periodically adjust the first distance (number of rotations) and/or the second distance (number of rotations). In some instances, it is contemplated that the controller 350 may periodically adjust a time period between driving the drive mechanism in the first rotational direction and driving the drive mechanism in the second rotational direction. For example, as shown, the controller 350 is driving the drive mechanism a little over 200 rotations in a first direction, and perhaps about 125 rotations in the second opposing direction. In some cases, the zero point may be chosen such that at the zero point, the drive motor 304 needs zero torque in order to maintain position. As illustrated, the time period between driving in the first direction and driving in the second direction is about 5 seconds. The controller 350 could, for example, vary the distance (number of rotations) in the positive direction between 150 and 250 rotations and perhaps vary the distance (number of rotations) in the negative direction between 75 and 150 rotations. The controller 350 could vary the time period from perhaps about 2 seconds to about 10 seconds. These are just examples, and are not intended to be limiting in any fashion.

As illustrated, the graphed motor position shown in FIG. 7 represents an asymmetric sine wave. As will be appreciated, this may be achieved by operating the drive motor 302 at a constant or largely constant rotational speed when driving in the first direction and in the second direction. In some cases, it is contemplated that the drive motor 302 may operate at a varying speed when driving in the first direction and in the second direction. For example, the drive motor 304 may operate faster when initially driving in a particular direction in order to save time, and may operate slower when approaching the desired number of rotations.

In some cases, using a position reference limits speed. As position is controlled by the controller 350, there is no risk of breaking anything by overwinding the system in attempting to clear a jam. In some instances, by limiting the number of turns in either the first direction or the second direction, it will be appreciated that torque limits of the system may be maintained. In some cases, the frequency at which the drive motor 302 operates may be selected in order to maintain low speed limits once the burr becomes un-stuck and is able to once again rotate.

As noted, the atherectomy system 300 has a predetermined torque limit. It will be appreciated that the torque experienced at the atherectomy burr is a combination of the torque applied by the drive motor 302, dynamic effects of the drive cable 304 as well as the inertia of the atherectomy system 300. The predetermined torque limit has to be set in order to accommodate dynamic effects. When the atherectomy burr is jammed, i.e., not moving, the dynamic effects and the inertia are much reduced, if not substantially zero. Accordingly, when the atherectomy burr is not moving because it is jammed, the torque applied by the drive motor 302 may be temporarily increased above the predetermined torque limit.

In some cases, the second operating mode includes operating the atherectomy system 300 at low speed at a temporary torque value that exceeds the predetermined torque limit of the first operating mode while the atherectomy burr is not moving. For example, the temporary torque value may exceed the predetermined torque limit of the first operating mode by five percent, or by ten percent. In some cases, the temporary torque value may exceed the predetermined torque limit by twenty percent, or by thirty percent, or forty percent or fifty percent or more. In some instances, the controller 350 may pulse the drive motor 302 for a brief period of time, perhaps five seconds, ten seconds or twenty seconds, and then briefly stop before pulsing the drive motor 302 again. In some cases, the second operating mode may include temporarily exceeding the predetermined torque limit of the first operating mode while alternating driving the drive mechanism in a first rotational direction and driving the drive mechanism in a second rotational direction opposite that of the first rotational direction. As soon as the atherectomy burr begins to move, the controller 350 would revert back to the first operating mode in which the predetermined torque value is honored.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An atherectomy system, comprising:
an atherectomy burr;
a drive mechanism adapted to rotatably actuate the atherectomy burr;
a controller adapted to operate the drive mechanism in a first operating mode in which the atherectomy burr is operated at a speed reference and with a predetermined torque limit;
the controller adapted to determine when the atherectomy burr becomes stuck while in the first operating mode;
the controller further adapted to, when the atherectomy burr becomes stuck, actively operate the drive mechanism in a second operating mode in which the atherectomy burr is operated at a position reference.

2. The atherectomy system of claim 1, wherein when in the second operating mode, the controller is further adapted to alternate between actively driving the drive mechanism in a first rotational direction and actively driving the drive mechanism in a second rotational direction opposite that of the first rotational direction.

3. The atherectomy system of claim 2, wherein when in the second operating mode, the controller is further adapted to actively drive the drive mechanism in the first rotational direction for a first distance and to actively drive the drive mechanism in the second rotational direction for a second distance that is different from the first distance.

4. The atherectomy system of claim 3, wherein the first distance and the second distance are selected based on a known spring constant of the drive mechanism.

5. The atherectomy system of claim 3, wherein when in the second operating mode, the controller is further adapted to periodically adjust the first distance and/or the second distance.

6. The atherectomy system of claim 3, wherein when in the second operating mode, the controller is further adapted to periodically adjust a time period between actively driving the drive mechanism in the first rotational direction and actively driving the drive mechanism in the second rotational direction.

7. The atherectomy system of claim 2, wherein the second operating mode further comprises temporarily exceeding the predetermined torque limit of the first operating mode while alternating between actively driving the drive mechanism in the first rotational direction and actively driving the drive mechanism in the second rotational direction opposite that of the first rotational direction.

8. The atherectomy system of claim 1, wherein the second operating mode further comprises operating the atherectomy burr at low speed at a temporary torque value that exceeds the predetermined torque limit of the first operating mode while the atherectomy burr is not moving.

9. The atherectomy system of claim 8, wherein the temporary torque value exceeds the predetermined torque limit of the first operating mode by ten percent or more.

10. The atherectomy system of claim 8, wherein the temporary torque value exceeds the predetermined torque limit of the first operating mode by up to fifty percent.

11. The atherectomy system of claim 8, wherein when in the second operating mode, the controller reverts back to the first operating mode as soon as the atherectomy burr begins to move.

12. An atherectomy system, comprising:
an atherectomy burr;
a drive mechanism adapted to rotatably actuate the atherectomy burr;
a controller adapted to operate the drive mechanism using a speed reference;
the controller adapted to determine when the atherectomy burr becomes stuck;
the controller further adapted to, when the atherectomy burr becomes stuck, switch to a stuck burr mode in which the controller uses a position reference in alternating between actively driving the drive mechanism in a first rotational direction and actively driving the drive mechanism in a second rotational direction opposite that of the first rotational direction.

13. The atherectomy system of claim 12, wherein when in the stuck burr mode, the controller is further adapted to actively drive the drive mechanism in the first rotational direction for a first distance and to actively drive the drive mechanism in the second rotational direction for a second distance that is different from the first distance.

14. The atherectomy system of claim 13, wherein the first distance and the second distance are selected based on a known spring constant of the drive mechanism.

15. The atherectomy system of claim 13, wherein when in the stuck burr mode, the controller is further adapted to periodically adjust the first distance and/or the second distance.

16. The atherectomy system of claim 13, wherein when in the stuck burr mode, the controller is further adapted to periodically adjust a time period between actively driving the drive mechanism in the first rotational direction and actively driving the drive mechanism in the second rotational direction.

17. An atherectomy system, comprising:
an atherectomy burr;
a drive mechanism adapted to rotatably actuate the atherectomy burr;
a controller adapted to operate the drive mechanism using a speed reference and with a predetermined torque limit;
the controller adapted to determine when the atherectomy burr becomes stuck;
the controller further adapted to, when the atherectomy burr becomes stuck, to operate the drive mechanism at low speed at a temporary torque value that exceeds the predetermined torque limit while the atherectomy burr is not moving.

18. The atherectomy system of claim 17, wherein the temporary torque value exceeds the predetermined torque limit up to fifty percent.

19. The atherectomy system of claim 17, wherein the controller reverts to operating the drive mechanism in accordance with the speed reference and the predetermined torque limit as soon as the atherectomy burr begins to move.

* * * * *